(12) United States Patent
Macher et al.

(10) Patent No.: US 8,334,389 B2
(45) Date of Patent: Dec. 18, 2012

(54) PROCESS FOR THE PREPARATION OF PLEUROMUTILINS

(75) Inventors: Ingolf Macher, Wörgl (AT); Andreas Berger, Ebbs (AT); Martin De Cristoforo, Kramsach (AT)

(73) Assignee: Nabriva Therapeutics AG, Vienna (AT)

( * ) Notice: Subject to any disclaimer, the term of this patent is extended or adjusted under 35 U.S.C. 154(b) by 382 days.

(21) Appl. No.: 12/444,330

(22) PCT Filed: Oct. 3, 2007

(86) PCT No.: PCT/AT2007/000468
§ 371 (c)(1), (2), (4) Date: Apr. 3, 2009

(87) PCT Pub. No.: WO2008/040043
PCT Pub. Date: Apr. 10, 2008

(65) Prior Publication Data
US 2009/0253748 A1    Oct. 8, 2009

(30) Foreign Application Priority Data
Oct. 5, 2006  (EP) .................... 06121852

(51) Int. Cl.
*C07D 211/40*  (2006.01)
(52) U.S. Cl. ..................................... 546/216
(58) Field of Classification Search .................. None
See application file for complete search history.

(56) References Cited

U.S. PATENT DOCUMENTS
7,534,814 B2 * 5/2009 Ascher et al. ............. 514/511

FOREIGN PATENT DOCUMENTS
| EP | 0 421 364 A2 | 4/1991 |
| WO | 02/22580 A1 | 3/2002 |

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002.*
Rouhi, "The Right Stuff, from research and development to the clinic, getting drug crystals right is full of pitfalls", Chemical & Engineering News, Feb. 24, 2003, pp. 32-35.*
Database Caplus Chemical Abstracts Service, Columbus, Ohio, US; Database Accession No. 2001:101106, Abstract of Ascher et al.: "Preparation of Mutilin Derivatives for Pharmaceutical Use as Antibacterial", WO 2001009095.*

* cited by examiner

*Primary Examiner* — Karl J Puttlitz
(74) *Attorney, Agent, or Firm* — Workman Nydegger

(57) ABSTRACT

A process for the preparation of 14-O-[(N-(3-methyl-2-amino-butyryl-piperidinyl)sulfanyl) acetyl]mutilins of formula (I) feasible for large-scale production of high purity products, and wherein the carbon atom at the piperidine ring attached to the sulphur atom is either in the (S)-configuration or in the (R)-configuration, and a new crystalline form of 14-O-[(N-3-methyl-2-(R)-amino-butyryl-piperidine-3(S)-yl)sulfanyl)acetyl]mutilin-hydrochloride.

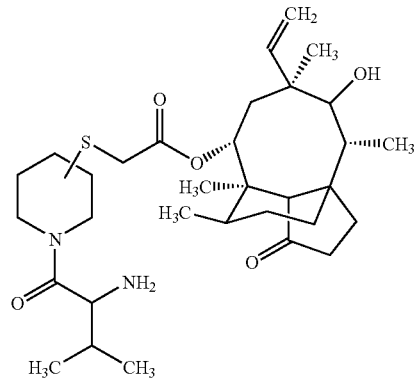

(I)

3 Claims, 1 Drawing Sheet

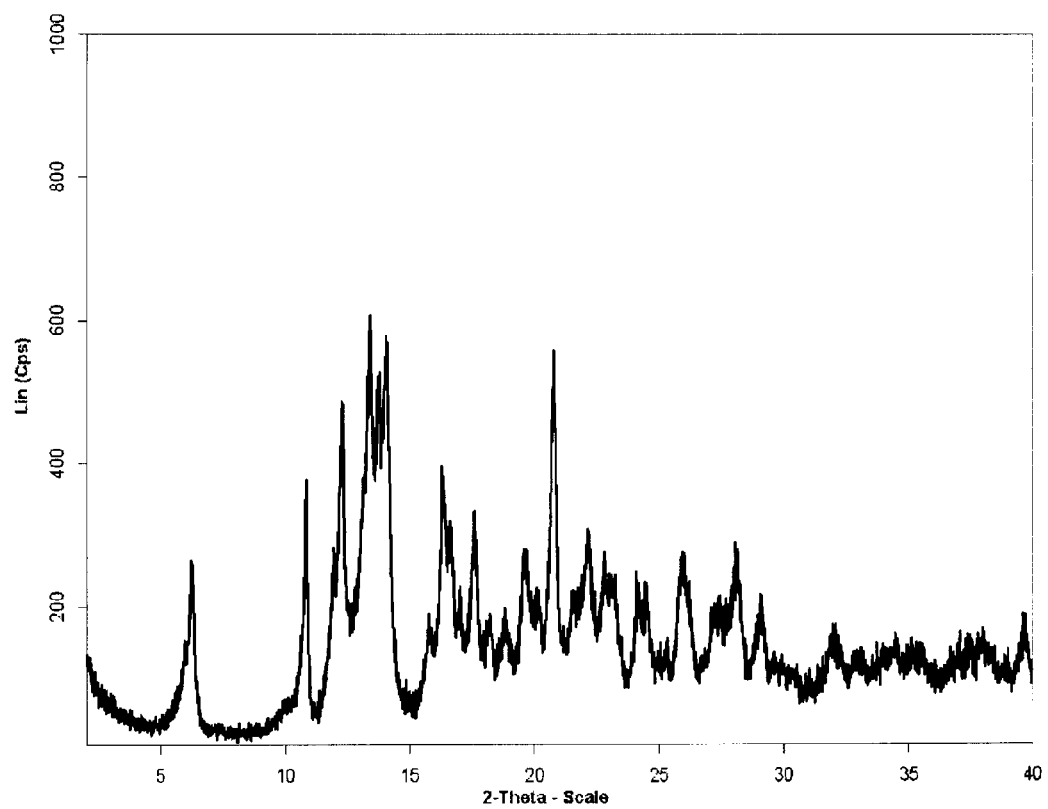

PROCESS FOR THE PREPARATION OF PLEUROMUTILINS

The present invention relates to a new process for the preparation of 14-O-[(N-(3-methyl-2-amino-butyryl-piperidinyl)sulfanyl)acetyl]mutilins.

Pleuromutilin, a compound of formula

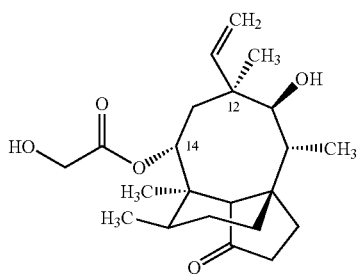

A is a naturally occurring antibiotic, e.g. produced by the basidomycetes *Pleurotus mutilus* and *P. passeckerianus*, see e.g. The Merck Index, 12th edition, item 7694. A number of further pleuromutilins having the principle ring structure of pleuromutilin and being substituted at the hydroxy group have been developed, e.g. as antimicrobials. Due to their pronounced antimicrobial activity, a group of pleuromutilin derivatives, valyl-substituted piperidineylsulfanylacetyl-mutilins, as disclosed in WO 02/22580, has been found to be of particular interest. For the production of substantially pure isomers of this group of compounds, a need is given to develop a process which is convenient to use in an industrial scale and avoids the application of costly starting materials, environmental hazardous reagents and solvents or time consuming and laborious purification steps, as well.

In one aspect the present invention provides a process for the preparation of a compound of formula

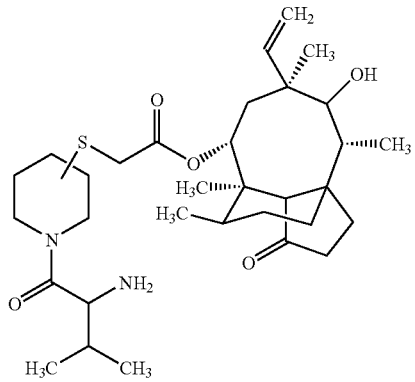

I wherein the carbon atom of the piperidine ring attached to the sulphur atom is either in the (S)-configuration or in the (R)-configuration and the 2-amino-3-methyl-butyryl group attached to the piperidine ring is either in the (S)-configuration or in the (R)-configuration, comprising the steps of a) deprotecting a N-protected piperidineylsulfanylacetyl-mutilin of formula

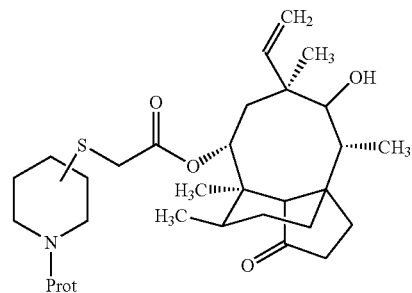

II and isolating a compound of formula

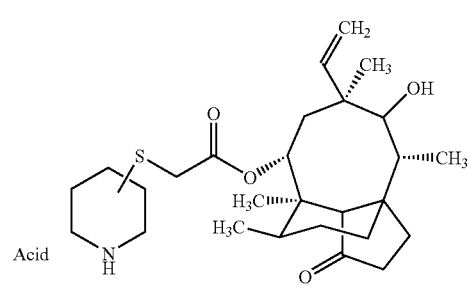

III wherein the carbon atom of the piperidine ring attached to the sulphur atom is either in the (S)-configuration or in the (R)-configuration, in free form or in the form of an acid addition salt, b) acylating said compound of formula III with either (R)- or (S)-valine protected as an enamine and activated as a carbonic acid mixed anhydride to form a compound of formula

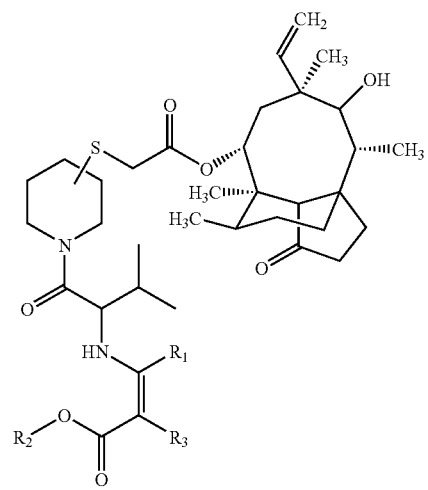

IV wherein $R_1$ and $R_2$ are $C_{1-4}$ alkyl, and $R_3$ is hydrogen or $C_{1-4}$ alkyl, c) deprotecting the compound of formula IV and isolating the compound of formula I.

In a preferred embodiment, the compound of formula I is isolated in the form of a pharmaceutically acceptable salt. In an even more preferred embodiment, the compound of formula I is isolated as a hydrochloride.

In a compound of formula I a carbon atom of the piperidine ring is bound to a sulphur atom. This bond may be in any position of the piperidine ring, e.g. in α, β or γ position, preferably in β position to the nitrogen atom of the piperidine ring.

BRIEF DESCRIPTION OF THE DRAWINGS

In order to describe the manner in which the advantages and features of the invention can be obtained, a particular description of the invention will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 is a powder diffractogram of 14-O-[(N-3-methyl-2-(R)-amino-butyryl-piperidine-3(S)-yl)sulfanyl)acetyl] mutilin hydrochloride.

Deprotection of the N-protected compound of formula II is effected by acidic cleavage of the protective group to form an acid addition salt as an isomeric mixture with respect to the configuration of the carbon atom of the piperidine ring attached to the sulphur atom in a compound of formula II. Preferably the configuration in the mutilin ring of a compound of formula II is the same as in a naturally produced mutilin. The isomeric mixture is conveniently separated via crystallisation in such a way that substantially pure isomers wherein the carbon atom of the piperidine ring attached to the sulphur atom is either in the (S)-configuration or in the (R)-configuration are obtained. The crystallisation step leads to a high purifying effect and the compound of formula III in crystalline form is therefore very suitable as an intermediate, particularly also on an industrial scale, in the process for producing piperidineylsulfanylacetylmutilins. In addition, usage of the compound of formula III in crystalline form has the advantage that other purification steps, such as chromatography, can be dispensed with, since the purity of the compound of formula III in crystalline form is completely sufficient for the production of valyl-substituted piperidineyl sulfanylacetylmutilins.

A mineral acid or an organic acid may be used to effect the deprotection of a compound of formula II. In a preferred embodiment, methanesulfonic acid is used to form the respective mesylate as an acid addition salt. As a protective group named as Prot in a compound of formula II conventional N-protecting groups may be used. Preferably, a tert. butoxycarbonyl group is employed.

It has been shown that by selecting an appropriate deprotecting agent, solubility of either the (S)-configuration or the (R)-configuration can selectively be enhanced in that isomeric (S)-configuration may be separated from the (R)-configuration. E.g., by using methanesulfonic acid as deprotecting agent the crystallized product is the pure (S)-isomer, whereas the (R)-isomer stays in solution (see Example 1F).

In a subsequent step, introduction of the valyl-moiety to the substantially pure isomer of the compound of formula III is effected by acylating said compound with either (R)- or (S)-valine protected as an enamine to form a compound of formula IV. The protected valine is produced by reacting either (R)- or (S)-valine with a β-keto ester of formula $R_1$—CO—CH($R_3$)—COOR$_2$ wherein $R_1$, $R_2$, and $R_3$ are as defined above. Preferably, acetoacetic acid methyl ester is used. Preferably, the valine is activated according to a mixed carbonic acid anhydride procedure. The mixed anhydride is produced in situ, e.g. with addition of pivalic acid chloride. After addition of the compound of Formula III produced in step a) a protected compound of formula IV is obtained. These compounds comprise superior crystallization properties in comparison with compounds having other protective groups, e.g. tert.-butoxycarbonyl. Compounds having these superior crystallization properties are easy to handle with regard to production and isolation and provide better opportunities for further purification, e.g. regarding 3-substituted piperidineylsulfanylacetylmutilins according to formula I the enamine protected compound according to formula IV is isolated and purified via crystallization whereas the corresponding tert.-butoxycarbonyl protected derivative has to be purified using tedious and laborious chromatography steps.

The protective group of compounds of formula IV is removed by acidic cleavage. After removal of the acetoacetic acid ester and extraction the compound according to formula I may be isolated in free form or, after addition of an acid which provides pharmaceutically acceptable salts and after lyophilization of the respective aqueous phase, in an amorphous form of a pharmaceutically acceptable salt, e.g. a hydrochloride.

In a preferred embodiment the carbon atom of the piperidine ring bound to the sulphur atom is in β-position to the nitrogen atom of the piperidine ring, that is a 3-substituted piperidineyl-sulfanylacetylmutilin of formula I. More preferably, the present invention is related to 14-O-[(N-3-methyl-2-(R)-amino-butyryl-piperidine-3(S)-yl)sulfanyl)acetyl] mutilin hydrochloride.

The present invention further relates to a novel crystalline form of 14-O-[(N-3-Methyl-2-(R)-amino-butyryl-piperidine-3(S)-yl)sulfanyl)acetyl]mutilin hydrochloride. The lyophilized amorphous compound of 14-O-[(N-3-methyl-2-(R)-amino-butyryl-piperidine-3(S)-yl) sulfanyl)acetyl]mutilin hydrochloride obtained via the reaction sequence described above is converted to a crystalline form using a crystallization process in an aqueous medium. The process may be enhanced and accelerated by the use of seed crystals. Via recrystallisation crystalline 14-O-[(N-3-methyl-2-(R)-amino-butyryl-piperidine-3(S)-yl)sulfanyl)acetyl]mutilin hydrochloride may be brought to a form of desired consistence and chemical and optical purity. Substantially pure isomers having a diastereomeric excess of ≧97% with regard to the 3-(S)-position are thus obtained.

Crystalline 14-O-[(N-3-methyl-2-(R)-amino-butyryl-piperidine-3(S)-yl)sulfanyl)acetyl]mutilin hydrochloride is characterized by an X-ray powder diffraction pattern with peaks 2-theta at 6.2±0.2, 10.9±0.2, 12.3±0.2, 13.4±0.2, 14.1±0.2, 20.8±0.2 degrees (2-theta, CuK-alpha). It may also be characterized by an infrared spectrum having characteristic bands at about 2927, 1721, 1645, 1462, 1403, 1142 cm$^{-1}$.

FIG 1: Powder diffractogram of 14-O-[(N-3-methyl-2-(R)-amino-butyryl-piperidine-3(S)-yl)sulfanyl)acetyl] mutilin hydrochloride In a crystalline form, 14-O-[(N-3-methyl-2-(R)-amino-butyryl-piperidine-3(S)-yl)sulfanyl)acetyl] mutilin hydrochloride provides higher purity and better stability than the amorphous lyophilized form, which is of advantage in the preparation of pharmaceutical compositions containing crystalline 14-O-[(N-3-methyl-2-(R)-amino-butyryl-piperidine-3(S)-yl)sulfanyl)acetyl] mutilin hydrochloride as an active ingredient.

N-protected piperidineylsulfanylacetylmutilins of formula II may be prepared by reacting a 14-O-mercaptoacetyl-mutilin with a N-protected hydroxypiperidine having a leaving group in α, β or γ position of the nitrogen atom of the piperidine ring, e.g. N-BOC-3(R)-methylsulfonyloxy-piperidine, s disclosed in WO 02/22580.

More conveniently, and as another aspect of the present invention, N-protected piperidineylsulfanylacetylmutilins may be prepared by reacting a pleuromutilin-22-O-sulfonate (e.g. mesylate, besylate or tosylate) with a N-protected piperidine thiol. Protection groups include appropriate protection groups, e.g. protection groups as conventional.

Preferably, a tert.-butoxycarbonyl group is used as N-protecting group and in another preferred embodiment, N-protected piperidine having the thiol group in 3-position of the piperidine ring is used. Racemic or enantiomerically pure N-protected piperidine thiol having either the (R)- or the (S)-configuration at the carbon atom bearing the thiol group may be used.

Preferably, N-protected piperidine thiol is used as a racemate to avoid the use of expensive chiral starting materials. The N-protected piperidine thiol may be prepared starting with the appropriate hydroxypiperidine by adding a N-protecting group (e.g. tert. butoxycarbonyl) and reacting with a sulfonic acid chloride or anhydride (e.g. methanesulfonyl chloride). The thiol group is introduced via reaction with a sulfur containing nucleophile, e.g. a thioacetate, and basic cleavage of the corresponding thioester (e.g. N-BOC-3-(R,S)-acetylthio-piperidine).

If the hydroxypiperidine is used in the form of a single enantiomer (e.g. 3-(R)-hydroxypiperidine), the reaction sequence outlined above including nucleophilic substitution using a thioacetate takes place in a controlled manner (Walden inversion) to produce the corresponding N-protected piperidine thiol wherein the carbon atom of the piperidine ring attached to the sulphur atom is either in the (S)-configuration or in the (R)-configuration (e.g. 3-(S)-piperidine thiol).

Further reaction with a pleuromutilin-22-O-sulfonate provides N-protected piperidineyl sulfanylacetyl mutilins of formula II wherein the carbon atom of the piperidine ring attached to the sulphur atom is either in the (S)-configuration or in the (R)-configuration.

In the following examples which illustrate the invention references to temperature are in degrees Celsius.

The following abbreviations are used:
N-BOC=N-butoxycarbonyl
RT=room temperature
MTBE=methyl tert.-butyl ether The numbering of the mutilin cyclus referred to in the examples is given in the following formula:

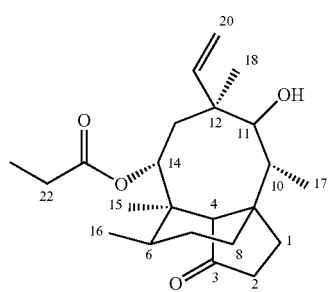

EXAMPLES

Example 1

14-O-[(N-3-Methyl-2-(R)-amino-butyryl-piperidine-3(S)-yl)sulfanyl)acetyl]mutilin hydrochloride A. N-BOC-3-(R,S)-Hydroxy-piperidine 202.4 g of 3-(R,S)-hydroxypiperidine are dissolved in 4,5 l of deionised water in a 10 l reactor. 336 g of sodium hydrogencarbonate, dissolved in 1.1 l water are added. To the vigorously stirred solution 534 g of di-tert.-butyl-dicarbonate are added at room temperature. After stirring overnight the mixture is extracted with $CH_2Cl_2$ (3×). The combined extracts are washed with deionised water and the solvent is distilled off. The residue is dissolved in $CH_2Cl_2$ again and the solution is evaporated to dryness. 423 g of N-BOC-3(R,S)-hydroxy-piperidine are obtained which can be used in the next step without further purification.

B. N-BOC-3-(R,S)-Methylsulfonyloxy-piperidine

To a solution of 216 g of N-BOC-3(R,S)-hydroxypiperidine in 5 l of $CH_2Cl_2$ 222 ml of triethylamine are added at 0-5° C. 137 g of methanesulfonyl chloride in 300 ml of $CH_2Cl_2$ are added dropwise over a period of 45 min, maintaining the temperature at 0-5° C. After additional stirring for 70 minutes 2 l of deionised water are added and the pH is adjusted to 5.9 by addition of about 90 ml of 2 n HCl. The aqueous phase is separated and the organic phase is washed with water. The solution is evaporated to dryness and 270-280 g of an oily residue are obtained. After treating with 1 l of n-heptane crystallization occurs. Crystals are isolated and dried in vacuo. 250 g of N-BOC-3(R,S)-methylsulfonyloxy-piperidine are obtained.

Mp.: 69° C.
$^1H$ NMR($CDCl_3$): 4.71 (m,1H,$CHOSO_2CH_3$), 3.2-3.6 (m,4H,CHN), 3.05 (s,3H,$CH_3SO_2$), 1.94 (m,2H,H4), 1.83, 1.54 (2 xm,2H,H5), 1.46 (m,9H, tert.-butyl).

C. N-BOC-3-(R,S)-Acetylthio-piperidine 2.7 l of dimetylformamide are placed in a reactor under inert atmosphere. 251.4 g of N-BOC-3(R,S)-methylsulfonyloxy-piperidine are added with warming. At an internal temperature of 50° C. 256.8 g of potassium thioacetate are added at once. After stirring for 90 min at 95° C. the reaction mixture is transferred into a reactor filled with 4 l of water. 4.2 l of petroleum ether are added. After vigorous stirring for 5 minutes the aqueous phase is removed. After readdition of water the pH is adjusted to >8 with sodium hydroxide. The organic phase is separated, washed with water and treated with active charcoal. The solution is evaporated to dryness. After flash chromatography on silica with petroleum ether, toluene, and ethyl acetate and concentration of the product containing solution crystallization occurs on cooling and 110 g of N-BOC-3(R,S)-acetylthio-piperidine are obtained.

Mp.: 46-48° C. (n-heptane)
$^1H$ NMR($CDCl_3$): 3.79 (dd, 1H, H2), 3.5-3.6 (m, 2H, H3, H6), 3.17-3.27 (m, 2H, H2, H6), 2.32 (s, 3H, $CH_3SO_2$), 1.99 (m, 1H, H4), 1.55-1.72 (m, H4, H5), 1.47 (s, 9H, tert.-butyl).

D. N-BOC-Piperidine-3-(R,S)-thiol 200 g of N-BOC-3(R,S)-acetylthio-piperidine are placed in a 10 l reactor with 3.4 l of methanol in an inert atmosphere. To this solution 42 g of sodium methoxide in methanol is added over a period of 15 min. After additional stirring 170 ml of 5 n HCl are added, bringing the pH-value to 2.6-3. The solution is concentrated at an evaporator. The resulting biphasic mixture is taken up with 1.7 l of methyl tert.-butyl ether (MTBE) and 1.7 l of water. After shaking, separation of the aqueous phase and washing the MTBE phase is isolated and evaporated, yielding 170 g of an oil.

$^1$H NMR(DMSO-d$_6$): 3.92 (b, 1H, H6), 3.69 (d, 1H, H2), 2.7-2.9 (m, 3H, H2, H3, H6), 2.61 (d, 1H, SH), 2.00 (m, 1H, H4), 1.64 (m, 1H, H5), 1.45-1.31 (m, 2H, H4, H5), 1.39 (s, 9H, tert.-butyl).

E. 14-O-[(N-BOC-Piperidine-3-(R,S)-yl)-sulfanylacetyl]-mutilin 359.7 g of 22-O-pleuromutilintosylate are suspended in 3.2 l of MTBE. 1350 ml of 1 n sodium hydroxide and 21.1 g of benzyl-tributylammonium chloride are added. The mixture is cooled to 15° C. and a solution of 161.6 g N-BOC-piperidine-3(R,S)-thiol in 800 ml of MTBE is added dropwise. The biphasic reaction mixture is stirred for one hour at 20° C.

After completion of the reaction the phases are separated. The organic phase is dried and evaporated to yield 521.5 g of 14-O-[(N-BOC-piperidine-3(R,S)-yl)-sulfanylacetyl]-mutilin as an oil which is used in the next step without further purification.

$^1$H NMR(CDCl$_3$):6.48 (dd, 1H, H19, J=17.4 Hz, J=11.2 Hz),5.77 (d, 1H, H14, J=8.4 Hz), 5.34, 5.20 (2 xdd, 2H, H20, J=11.2 Hz, J=1.3 Hz; J=17.4 Hz, J=1.3Hz), 4.0, 3.75, 2.96, 2.01 (b, 6H, piperidine), 3.37 (dd, 1H, H11, J=10.5 Hz, J=6.6 Hz), 3.19 (m, 2H, SCH$_2$), 2.85 (m, 1H, CHS), 2.36 (dq, 1H, H10, J=6.6 Hz, J=6.5 Hz), 2.11 (b, 1H, H4) 1.47 (s, 12H, (CH$_3$)$_3$,(CH$_3$)15), 1.18 (s, 3H, (CH$_3$)18), 0.89 (d, 3H, (CH$_3$) 17, J=6.9 Hz), 0.75 (d, 3H, (CH$_3$)16, J=6.5 Hz).

F. 14-O-[(Piperidine-3-(S)-thioacetyl)]-mutilin methanesulfonate 521 g of 14-O-[(N-BOC-piperidine-3(R,S)-yl)-sulfanylacetyl]-mutilin are dissolved in 4 l of 2-propanol and heated to 55° C. After addition of 165 ml of methanesulfonic acid the solution is stirred for 5 h at this temperature. After completion of cleavage of the BOC-group the reaction mixture is cooled to 0° C. and stirred for another 2 h. The crystallized product is filtered off, washed with 2-propanol and dried in vacuo. 159.8 g of 14-O-[(Piperidine-3(S)-thioacetyl)]-mutilin methanesulfonate are obtained.

Mp.: 250-255° C. $^1$H NMR(DMSO-d$_6$): 8.58 (m, 2H, NH$_2^+$), 6.15 (dd, 1H, H19, J=17.2 Hz, J=11.5 Hz), 5.57 (d, 1H, H14, J=8.2 Hz), 5.07 (m, 2H, H20), 4.5 (b, 1H, OH), 3.41 (s, 2H, SCH$_2$), 2.4 (b, 1H, H4), 2.32 (s, 3H, CH$_3$SO$_3^-$), 1.37 (s, 3H, (CH$_3$)15), 1.07 (s, 3H, (CH$_3$)18), 0.83 (d, 3H, (CH$_3$) 17, J=7.0 Hz), 0.64 (d, 3H, (CH$_3$)16, J=6.6 Hz).

G. N-(3-Methoxy-1-methyl-3-oxo-1-propenyl)-R-valine, potassium Dane salt (R-valine Dane salt)

36.6 g solid KOH are dissolved in 1250 ml of 2-propanol with slight warming. 65 g R-valine and 65.9 ml of methyl acetoacetate are added. The mixture is stirred and refluxed for 2 h. The reflux condenser is replaced by a Claisen condenser and a short column and the water formed during the condensation reaction is removed by distilling off about 1 l 2-propanol. Thereafter 500 ml of 2-propanol are added and again 500 ml are distilled off. The warm solution is poured into 3 l of MTBE and stirred with ice-cooling for about 3 h. The resulting suspension is left overnight at 4° C. (moisture excluded), filtered, washed with 500 ml of MTBE and dried to yield N-(3-methoxy-1-methyl-3-oxo-1-propenyl)-R-valine potassium salt.

H. 14-O-[(N-(3-Methyl-2-(R)-N-(3-methoxy-1-methyl-3-oxo-1-propenyl-amino)-butyryl)-piperidine-3-(S)-yl)-sulfanylacetyl]-mutilin (Dane compound)

To a suspension of 88.2 g of R-valine Dane salt in 2175 ml of MTBE 14.5 ml of water are added and the mixture is stirred for 10 min at room temperature. The mixture is cooled to 0° C. and 3.5 ml 4-methylmorpholine and 41 ml pivaloyl chloride are added and stirred for 1 h. 2175 ml of precooled water (0-4° C.) and 166.4 g 14-O-[(Piperidine-3(S)-thioacetyl)]-mutilin methanesulfonate are added. The pH-value of the mixture is kept at 7.0 by addition of about 210 ml of 2 n NaOH. The cooled mixture (0° C.) is stirred for 30 min, whereby crystallization of the Dane compound occurs. For completion of reaction, the suspension is warmed to 30° C. and stirred for 1 h. Afterwards the pH-value is set to 9.5 by addition of about 85 ml of 2 n NaOH. After cooling to 0° C. and stirring for another 2 h the crystals are filtered off, washed with cooled water and MTBE and dried in vacuo. 195.4 g of Dane compound as MTBE-solvate are obtained.

Mp.: 136-142° C.

$^1$H NMR (DMSO-d$_6$, 1:1 mixture of two stable rotamers): 8.87, 8.83 (2 xd, 1H, NH, J=9.3 Hz), 6.15 (m, 1H, H19), 5.60, 5.56 (2 xd, 1H, H14, J=8.3 Hz), 5.04 (m, 2H, H20), 4.50 (m, 1H, α-H-Val), 4.37 (s, 1H, CH-enamine), 3.50 (s, 3H, OCH$_3$), 2.42, 2.40 (2 xb, 1H, H4), 1.87, 1.85 (2 xs, 3H, CH$_3$-enamine), 1.36 (2 xs, 3H, (CH$_3$)15), 1.07 (s, 3H, (CH$_3$) 18), 0.96-0.77 (m, 9H, (CH$_3$)17, (CH$_3$)$_2$Val), 0.64 (m, 3H, (CH$_3$)16).

I. 14-O-[(N-3-Methyl-2-(R)-amino-butyryl-piperidine-3(S)-yl)sulfanyl)acetyl]mutilin hydrochloride 145 g of Dane compound are suspended in a mixture of 1.8 l of MTBE and 1.8 l of water. The mixture is warmed to about 50° C. and vigorously stirred. The pH-value is kept at 1.0 by dropwise addition of 2 n HCl. The completion of the cleavage of the enamine protecting group is followed by HPLC. The organic phase is separated and the aqueous phase is extracted twice with MTBE (1.6 l each) to remove methyl acetoacetate. To the stirred aqueous phase 1.6 l of MTBE are added and the pH is adjusted to 10 by addition of 10 n NaOH. Phases are separated and the MTBE phase is extracted twice with 1.6 l portions of water. After addition of 1.5 l of water the pH is adjusted to 3.2 by addition of about 100 ml of 2 n HCl. The aqueous phase is concentrated in a rotary evaporator. Lyophilisation of the remaining solution yields 117.4 g of title compound.

$^1$H NMR (DMSO-d$_6$, ~1:1 mixture of two stable rotamers): 7.95 (b, 3H, NH$_3^+$), 6.15 (dd, 1H, H19, J=17.6 Hz, J=11.2 Hz), 5.6 (d, 1H, H14, J=8.2 Hz), 5.05 (m, 2H, H20), 4.53 (m, 1H, OH), 4.24,4.30 (2 xd, 1H, α-H-Val, J=4.8 Hz), 4.08 (dd, 0.5H, H2-piperidine, J=13.7 Hz, J=3.3 Hz), 3.08 (dd, 0.5 Hz, H2-piperidine, J=13.7 Hz, J=9.8 Hz), 3.89 (dd, 0.5H, H2-piperidine, J=13.1 Hz, J=3.2 Hz), 3.41 (m, 0.5H, H2-piperidine), AB-System: Fehler! Es ist nicht möglich, durch die Bearbeitung von Feldfunktionen Objekte zu erstellen.$_A$=3.44, Fehler! Es ist nicht möglich, durch die Bearbeitung von Feldfunktionen Objekte zu erstellen.$_B$=3.33 (2H, SCH$_2$, J=14.9 Hz), 3.42 (m, 1H, H11), 2.83, 2.96 (2 xm, 1H, CHS), 2.4 (b, 1H, H4), 1.34 (s, 3H, (CH$_3$)15), 1.05 (s, 1H, (CH$_3$)18), 0.9, 1.0 (2 xm, 6H, (CH$_3$)$_2$Val), 0.81 (d, 3H, (CH$_3$) 17, J=6.9 Hz), 0.63 (m, 3H, (CH$_3$)16).

Example 2

Crystalline form of 14-O-[(N-3-Methyl-2-(R)-amino-butyryl-piperidine-3-(S)-yl)sulfanyl)acetyl] mutilin hydrochloride 3.0 l of water are placed in a reactor and warmed to 40° C. 1 kg of lyophilized 14-O-[(N-3-methyl-2-(R)-amino-butyryl-piperidine-3(S)-yl)sulfanyl)acetyl]mutilin hydrochloride are added and the addition device is rinsed with 1.0 l of water. After approximately 10 minutes a pale yellow solution is obtained. The solution is seeded and slowly stirred at 40° C. for 6 hours. Then the heating is stopped and the crystal suspension is stirred at ambient temperature for another 64 hours. The product is filtered, washed with 1.5 l of cold water and recrystallised without drying or the wet product is dried at 40° C. in vacuo, yielding 819 g of crystalline title compound.

Recrystallisation 1.5 l of water are placed in a reactor and warmed to 50° C. The wet product of the first crystallisation is added and the addition device is rinsed with 1.0 l of water. The suspension is heated to 70-75° C. until the product is dissolved. The solution is cooled, seeded and slowly stirred at 40° C. for 6 hours. Then the heating is stopped and the crystal suspension is stirred at ambient temperature for another 24 hours. The product is filtered, washed with 1.3 l of cold water and dried at 40° C. in vacuo, yielding 765 g of crystalline title compound.

Mp.: 150-155° C.

The invention claimed is:

1. Crystalline 14-O-[(N-3-methyl-2-(R)-amino-butyryl-piperidine-3(S)-yl)sulfanyl)acetyl]mutilin hydrochloride with XRD peaks 2-theta of Angle (2-Theta)
6.2±0.2
10.9±0.2
12.3±0.2
13.4±0.2
14.1±0.2
20.8±0.2, and having a 3-(S)-diastereomeric excess of ≧97%.

2. Process for preparation of crystalline compound of claim 1, comprising the steps of dissolving and warming 14-O-[(N-3-Methyl-2-(R)-amino-butyryl-piperidine-3(S)-yl)sulfanyl)acetyl]mutilin hydrochloride in an aqueous medium optionally seeding the solution and stifling at elevated temperature cooling the obtained suspension and stifling at ambient temperature isolating crystalline product and optionally repeating the procedure.

3. Pharmaceutical compositions containing crystalline 14-O-[(N-3-methyl-2-(R)-amino-butyryl-piperidine-3(S)-yl)sulfanyl)acetyl]mutilin-hydrochloride with XRD peaks 2-theta of Angle (2-Theta)
6.2±0.2
10.9±0.2
12.3±0.2
13.4±0.2
14.1±0.2
20.8 ±0.2 and having a 3-(S)-diastereomeric excess of ≧97%.

* * * * *